United States Patent
Kim

(10) Patent No.: US 12,295,887 B2
(45) Date of Patent: May 13, 2025

(54) OPHTHALMIC TREATMENT DEVICE AND CONTROL METHOD THEREFOR

(71) Applicant: LUTRONIC CORPORATION, Goyang (KR)

(72) Inventor: Jong Min Kim, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 104 days.

(21) Appl. No.: 17/681,451

(22) Filed: Feb. 25, 2022

(65) Prior Publication Data

US 2022/0175578 A1 Jun. 9, 2022

Related U.S. Application Data

(63) Continuation of application No. 16/320,984, filed as application No. PCT/KR2017/007961 on Jul. 24, 2017, now Pat. No. 11,266,529.

(51) Int. Cl.
*A61F 9/009* (2006.01)
*A61F 9/008* (2006.01)
(Continued)

(52) U.S. Cl.
CPC .............. *A61F 9/009* (2013.01); *A61F 9/008* (2013.01); *A61F 9/00814* (2013.01);
(Continued)

(58) Field of Classification Search
CPC .. A61F 2009/00844; A61F 2009/00851; A61F 2009/00868; A61F 2009/00891;
(Continued)

(56) References Cited

U.S. PATENT DOCUMENTS 10,588,781 B2 * 3/2020 Kim ................... A61F 9/00821
2006/0111697 A1 5/2006 Brinkmann
(Continued)

FOREIGN PATENT DOCUMENTS

JP 2008161226 A 7/2008
JP 2008183247 A 8/2008
(Continued)

OTHER PUBLICATIONS

International Search Report for PCT/KR2017/007961 mailed Nov. 2, 2017.

*Primary Examiner* — Scott Luan

(57) ABSTRACT

The present invention relates to an ophthalmic treatment apparatus and a control method therefor, and provides an ophthalmic treatment apparatus and a control method therefor, the ophthalmic treatment apparatus comprising: a setting unit formed so as to set a treatment mode; a therapeutic light emission unit emitting therapeutic light at a target position of an eyeground multiple times so as to perform treatment; a monitoring unit for monitoring information on the state of the target position by the therapeutic light during the emission of the therapeutic light; and a control unit for determining whether a treatment intensity according to the treatment mode has been reached, by using the information monitored by the monitoring unit, and for controlling an operation of the therapeutic light emission unit on the basis of the determination.

20 Claims, 16 Drawing Sheets

(51) Int. Cl.
*A61N 5/06* (2006.01)
*A61N 5/10* (2006.01)

(52) U.S. Cl.
CPC ...... *A61F 9/00821* (2013.01); *A61F 9/00823* (2013.01); *A61F 9/0084* (2013.01); *A61N 5/06* (2013.01); *A61F 2009/00844* (2013.01); *A61F 2009/00851* (2013.01); *A61F 2009/00868* (2013.01); *A61F 2009/00891* (2013.01); *A61N 5/1028* (2013.01)

(58) Field of Classification Search
CPC .. A61F 9/008; A61F 9/00814; A61F 9/00821; A61F 9/00823; A61F 9/0084; A61F 9/009
See application file for complete search history.

(56) References Cited

U.S. PATENT DOCUMENTS

| | | | |
|---|---|---|---|
| 2007/0213693 A1* | 9/2007 | Plunkett | A61F 9/008 606/4 |
| 2008/0188838 A1 | 8/2008 | Abe | |
| 2017/0216090 A1 | 8/2017 | Kim | |
| 2017/0266041 A1 | 9/2017 | Kim et al. | |

FOREIGN PATENT DOCUMENTS

| | | |
|---|---|---|
| KR | 1020140009846 A | 1/2014 |
| KR | 1020150128624 A | 11/2015 |
| KR | 1020160015044 A | 2/2016 |
| WO | WO2004065923 A1 | 8/2004 |

* cited by examiner

OPHTHALMIC TREATMENT DEVICE AND CONTROL METHOD THEREFOR

CROSS-REFERENCE TO RELATED APPLICATIONS

The present specification is a continuation of U.S. application Ser. No. 16/320,984 filed on Jan. 25, 2019, now U.S. Pat. No. 11,266,529, which is a U.S. National Stage of International Patent Application No. PCT/KR2017/007961 filed Jul. 24, 2017, which claims priority to and the benefit of Korean Patent Application No. 10-2016-0095495 filed in the Korean Intellectual Property Office on Jul. 27, 2016, the entire contents of which are incorporated herein by reference.

TECHNICAL FIELD

The present invention relates to an ophthalmic treatment apparatus and a control method therefor, and more particularly, to an ophthalmic treatment apparatus that controls how treatment is going by detecting the state of a target site during treatment, and a control method therefor.

BACKGROUND ART

Nowadays, there are technologies widely used to perform treatment by inducing changes in human tissue state by light irradiation so as to deliver energy to the tissue. They are widely used especially for the treatment of lesions with a laser.

Many ophthalmic treatment apparatus using laser are being developed, including apparatus for treating diseases of the anterior segment of the eye for use in keratoplasty, glaucoma surgery, cataract surgery, etc., and new apparatus are being developed today that will treat various diseases of the fundus, including macular degeneration. An ophthalmic surgical apparatus of this type is disclosed in Korean Patent Laid-Open Publication No. 10-2014-0009846.

Such a treatment apparatus performs treatment by inducing changes in tissue by energy delivered to a target site through light. However, delivering an excessive amount of energy to the target site may damage the target tissue and neighboring tissues, and may result in loss of vision, especially in the treatment of ophthalmic diseases. Thus, it is necessary to monitor how treatment is going during treatment, but there are limitations in detecting minute changes in tissue.

DISCLOSURE

Technical Problem

The present invention is directed to providing an optical treatment apparatus that can monitor, in real time, changes in tissue state in a treatment area during treatment and perform treatment based on these changes.

Technical Solution

An exemplary embodiment of the present invention provides an ophthalmic treatment apparatus comprising: an ophthalmic treatment apparatus comprising: a setting unit formed so as to set a treatment mode; a treatment beam irradiation unit for irradiating a target site at the fundus with a treatment beam multiple times so as to perform treatment; a monitoring unit for monitoring information on the state of the target site caused by the treatment beam during the treatment beam irradiation; and a control unit for determining whether a treatment intensity according to the treatment mode is reached, by using the information monitored by the monitoring unit, and for controlling an operation of the treatment beam irradiation unit on the basis of the determination.

For example, if it is determined that the information detected by the monitoring unit does not reach the set treatment intensity, the control unit may adjust the parameters of treatment beams, and if it is determined that the information detected by the monitoring unit reaches the set treatment intensity, the control unit may terminate irradiating the target site with a treatment beam.

Here, the treatment beam is focused to a spot size enough to deliver energy to a plurality of RPE cells located at the target site, and some of the RPE cells undergo state changes by being irradiated with a plurality of beams, along with the progress of the treatment. Specifically, the treatment beam may be focused to a spot size enough to deliver energy to at least 60 RPE cells. Alternatively, the treatment beam may be focused to a spot size having a diameter of 50 µm or greater at the fundus.

Also, the monitoring unit may be configured to detect the amount of RPE cells whose state has changed by treatment, out of the plurality of RPE cells located at the target site being irradiated with the treatment beam, and monitor the treatment intensity for the target site.

Here, the monitoring unit may be configured using an optoacoustic sensor or reflectometry sensor. Alternatively, the monitoring unit may include a first monitoring unit configured as an optoacoustic sensor and a second monitoring unit configured as a reflectometry sensor, wherein, if it is determined that the set treatment intensity is reached based on information monitored by at least one of the first and second monitoring units, irradiating the target site with a treatment beam may be terminated.

The setting unit may be configured to indicate a plurality of treatment intensities of different values and allow the user to select a treatment intensity and set a treatment mode, or may be configured to indicate a plurality of diseases and allow the user to select a disease to be treated and set a treatment mode.

Another exemplary embodiment of the present invention provides a control method for an ophthalmic treatment apparatus, the control method comprising: selecting a treatment intensity through a setting unit; irradiating a target site where a plurality of RPE cells are located with a treatment beam; monitoring information on changes in the state of the plurality of RPE cells located at the target site through a monitoring unit; determining whether the set treatment intensity is reached, based on the monitored information; and if it is determined that the set treatment intensity is not reached, adjusting the parameters of treatment beams in such a way that the amount of energy delivered per unit area of the target site increases.

Yet another exemplary embodiment of the present invention provides an ophthalmic treatment apparatus comprising: a treatment beam irradiation unit for irradiating a target site at the fundus with a treatment beam multiple times; a first monitoring unit for monitoring information on the state of the target site by a first method during the treatment beam irradiation; a second monitoring unit for monitoring information on the state of the target site by a second method, different from the first method, during the treatment beam irradiation; and a control unit for adjusting the parameters of treatment beams or determining whether to irradiate with a treatment beam, based on information measured by the first monitoring unit and second monitoring unit.

Here, the first monitoring unit may measure information on how the treatment of the target site is going or the timing of completion of treatment, and the second monitoring unit may measure information on whether something unusual has occurred during treatment.

Advantageous Effects

According to the present invention, treatment intensity may be effectively controlled by performing treatment with energy delivered to a plurality of RPE cells located in a target area.

Another advantage is that optimal treatment may be performed by determining the timing of completion of treatment while monitoring how treatment is going in real time during treatment.

Moreover, it is possible to effectively monitor information on state changes during treatment by a monitoring unit for monitoring information on the state of tissue in different ways.

A further advantage is that it is possible to effectively deal with an unpredictable situation during treatment since the ophthalmic treatment apparatus is configured to decide if something unusual occurs during treatment and stop urgently in the event of an unusual occurrence.

MODE FOR INVENTION

Figure 1:
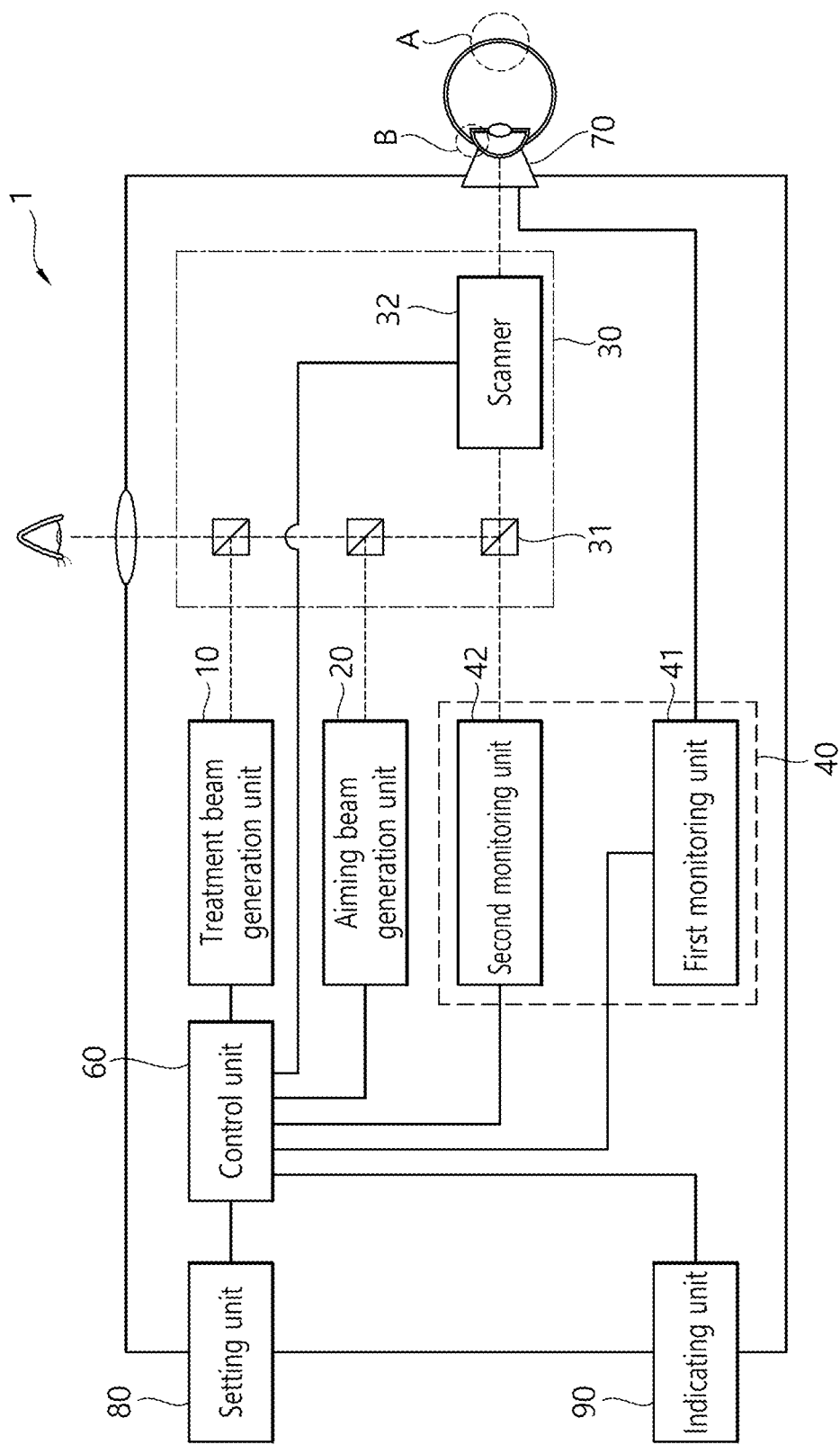
FIG. 1 is a schematic view schematically showing an ophthalmic treatment apparatus according to a first exemplary embodiment of the present invention.

Hereinafter, an ophthalmic treatment apparatus according to an exemplary embodiment of the present invention will be described in detail with reference to the drawings. In the following description, the positional relationship of each component is principally described based on the drawings. The structure of the invention in the drawings may be illustrated, for the convenience of description, as simplified or exaggerated if necessary. Therefore, the present invention is not limited thereto, and other than these, various apparatus may be, of course, added, changed, or omitted.

Although the ophthalmic treatment apparatus described below can be used as apparatus for treating diseases of the fundus and glaucomatous diseases of the anterior segment of the eye, the present invention may also be applied to apparatus for treating other diseases. For example, it may be applied to treat lesions of the skin tissue. Therefore, it should be noted that the present invention is not limited to the ophthalmic treatment apparatus to be described below, and it can be widely used as apparatus for the optical treatment of other diseases.

FIG. 1 is a schematic view schematically showing an ophthalmic treatment apparatus according to a first exemplary embodiment of the present invention. As shown in FIG. 1, an ophthalmic treatment apparatus according to the present invention includes a treatment beam generation unit 10 for generating a treatment beam, an aiming beam generation unit 20 for generating an aiming beam, and a beam delivery unit 30 for forming a travel path of the treatment beam and the aiming beam. Furthermore, the ophthalmic treatment apparatus further includes a monitoring unit 40 for detecting information on the tissue state of a target site being irradiated with the treatment beam and a control unit 60 for controlling various components based on the information detected by the monitoring unit.

The treatment beam generation unit 10 may be configured to include a treatment beam-light source and various optical elements for processing the characteristics of the light generated from the treatment beam-light source. The treatment beam is composed of a laser, and the treatment beam-light source may be configured to include a laser medium such as Nd:YAG, Ho:YAG or the like or a laser diode, capable of oscillating a laser. The treatment beam-light source is designed to emit a laser having a suitable wavelength, pulse width, and output power according to the characteristics of lesions or the characteristics of target tissue to which energy is transferred. Also, various apparatus such as various types of electric circuits for generating a laser, optical filters, shutters, etc. may be included to generate a laser.

The aiming beam generation unit 20 generates an aiming beam to be emitted onto the treatment area. The aiming beam is an element for indicating a point where a treatment beam is directed before or during treatment beam irradiation, so that the operator can identify that point. For example, the aiming beam may have a wavelength of visible light, and the operator may identify a treatment area by the aiming beam reflected from the treatment area.

The aiming beam generation unit 20 may direct an aiming beam to a single spot at a target site through the same path as the treatment beam. Alternatively, it is also possible to emit an aiming beam in a pattern consisting of a plurality of spots, so as to indicate a plurality of sites where the aiming beam is directed. Besides, the aiming beam may be emitted in the form of a lattice or boundary line to indicate an area where the treatment beam is directed.

However, if it is possible for the operator to identify a treatment area through a separate interface such as a monitor, the aiming beam generation unit may be omitted.

On the other hand, the beam delivery unit 30 is composed of a plurality of optical elements and constitutes an optical path through which the treatment beam travels. Also, the aiming beam, and a probe beam of a second monitoring unit which will be described later, also travel along the beam delivery unit. In this case, the aiming beam and the probe beam may be configured to share at least part of the optical path of the treatment beam, or, if necessary, may be configured to have their own separate optical path.

Specifically, the beam delivery unit 30 includes a plurality of beam combiners 31. By this, the treatment beam, the aiming beam, and the probe beam can respectively pass through the beam delivery unit 30 and be directed onto the treatment area, as shown in FIG. 1. Then, the aiming beam and probe beam reflected from the treatment area may be directed toward where the operator's eye is located through the beam delivery unit 30 or may be incident on the second monitoring unit 42 again.

The beam delivery unit 30 may include a scanner 32 for changing the location of beam irradiation. The scanner 32 is configured to include at least one reflecting mirror and a driving unit for rotating the reflecting mirror, so that the point where a beam is directed can be changed as the rotational position of the reflecting mirror from which the beam is reflected changes.

In addition, although not shown in specific details in the drawings, the beam delivery unit may be configured to further include optical elements such as a plurality of optical lenses for focusing or dispersing light, optical filters, etc.

An object part 70 may be provided at the end of the beam delivery unit 30. The object part 70 is a component where the patient's eye is to be treated is located, and includes a contact lens that comes into contact with the patient's eye. Further, a suction apparatus for sucking the patient's eye and fixing it in place may be included to fix the patient's eye during surgery.

As stated above, a treatment beam irradiation unit includes the treatment beam generation unit 10 and the beam delivery unit 30, and a treatment beam generated from the treatment beam generation unit 10 is directed to a treatment area within the eyeball through the beam delivery unit 30 and the object part 70. Also, an aiming beam irradiation unit includes the aiming beam generation unit 20 and the beam delivery unit 30, and an aiming beam generated from the aiming beam generation unit is directed to a treatment area at the fundus through the beam delivery unit 30 and the object part 70.

Figure 2:
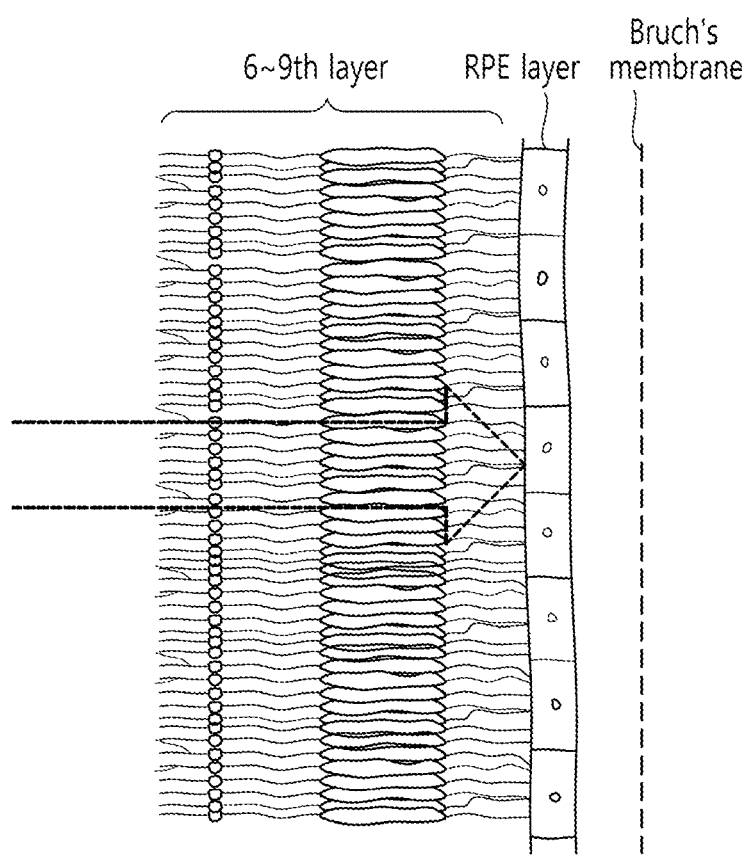
FIG. 2 is an enlarged cross-sectional view illustrating the area A of FIG. 1.

FIG. 2 is an enlarged cross-sectional view illustrating the area A of FIG. 1. A of FIG. 2 is a view of a patient's retinal tissue corresponding to a treatment area. The retinal tissue is generally made up of ten layers, including an internal limiting layer, a nerve fiber layer, a ganglion cell layer, an inner plexiform layer, an inner nuclear layer, an outer plexiform layer, an outer nuclear layer, an external limiting layer, a photoreceptor layer, and a retinal pigment epithelial (RPE) layer (from closest to farthest from the surface of the retina).

Among these ten layers, the RPE cell layer is a boundary layer at the back, and has tight junctions. A Bruch's membrane lies under the RPE layer. The RPE layer receives nutrients and oxygen from the blood vessels in the choroid and supplies these nutrients to the photoreceptors and transports metabolic waste from the photoreceptors across the Bruch's membrane.

If some of the RPE cells forming the RPE layer is unable to function normally, the photoreceptors located in front of these RPE cells die because they don't get enough nutrients and oxygen. To solve this problem, the ophthalmic treatment apparatus according to the present exemplary embodiment performs treatment by delivering energy to the RPE cells by treatment beam irradiation and inducing the generation of new RPE cells.

More specifically, a treatment beam generated by the treatment beam generation unit 10 has a wavelength in a visible light or near-infrared light region. Light with a corresponding wavelength passes through the cell layers (the first cell layer to the ninth cell layer) located in front of the retina, with little being absorbed in them, and then is absorbed into melanosomes existing in the RPE cells of the RPE cell layer. Therefore, as the amount of energy absorbed into the melanosomes increases, the temperature of the RPE cells rises, thus causing changes in cell state. Thus, the RPE cells whose state has changed are replaced with healthy RPE cells. It is understood that microbubbles are generated on the surface of the melanosomes as the temperature rises, and that the RPE cells are selectively necrotized as the microbubbles gradually grow.

As such, the ophthalmic treatment apparatus according to the present exemplary embodiment may perform treatment by targeting the retinal tissue to treat diseases of the fundus as explained with reference to FIG. 2, and may also treat diseases such as glaucoma by irradiating a treatment area located at the anterior segment of the eye with a treatment beam.

Figure 3:
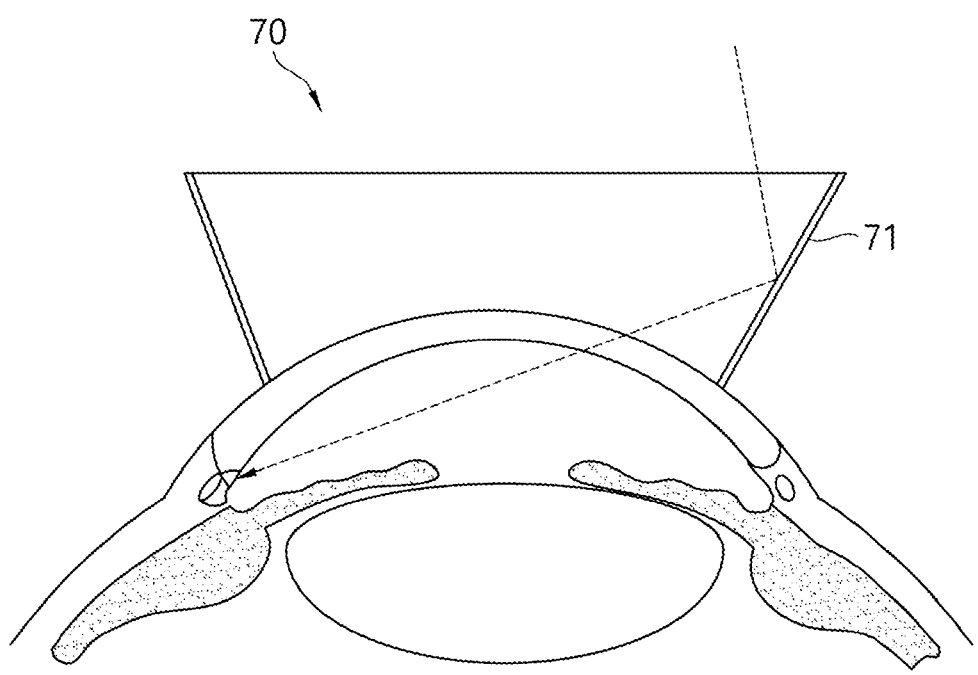
FIG. 3 is an enlarged cross-sectional view illustrating the area B of FIG. 1.

FIG. 3 is an enlarged cross-sectional view illustrating the area B of FIG. 1. Glaucoma is a group of eye diseases which results in damage to the optic nerve from increasing pressure within the eye, and treatment of glaucoma is performed by ensuring that passageways through which the intraocular fluid drains are opened up to maintain appropriate eye pressure. To this end, as shown in FIG. 3, the ophthalmic treatment apparatus according to the present exemplary embodiment may improve the fluid drainage characteristics by irradiating the trabecular meshwork (TM) tissue, located under the limbus of the anterior segment of the eye, with a treatment beam.

The trabecular meshwork tissue includes a plurality of trabecular meshwork cells. Like the above-described RPE cells, the trabecular meshwork cells (TM cells) contain pigments such as melanosomes. Accordingly, treatment is performed using a treatment beam with a wavelength that can be selectively absorbed by melanosomes, just like the way treatment is performed as explained with reference to FIG. 2. By treatment beam irradiation, energy is delivered to the cells in the trabecular meshwork tissue, and this causes thermal damage to the trabecular meshwork cells, thereby opening fluid passageways and maintaining eye pressure in a normal range.

That is, in the treatment of diseases of the fundus, the ophthalmic treatment apparatus performs treatment by targeting the retina and delivering energy to a plurality of RPE cells located at the target site, as shown in FIG. 2. On the other hand, in the treatment of diseases of the anterior segment of the eye, such as glaucoma, the ophthalmic treatment apparatus performs treatment by targeting trabecular meshwork tissue at the anterior segment of the eye and delivering energy to a plurality of trabecular meshwork cells located at the target site, as shown in FIG. 3.

Therefore, the object part 70 of the ophthalmic treatment apparatus includes a contact lens including a reflective member when treating the treatment area of FIG. 3. As such, various types of light, including a treatment beam, is directed to the target site, i.e., trabecular meshwork tissue, through the reflective member, and reflected light from the target site may enter the beam delivery unit of the ophthalmic treatment apparatus through the reflective member 71.

The ophthalmic treatment apparatus according to the present exemplary embodiment may be configured to treat either the treatment area of FIG. 2 or the treatment area of FIG. 3 or may be configured to treat both the treatment areas of FIGS. 2 and 3 by replacing the object part.

However, if a treatment beam delivers an excessive amount of energy during a treatment procedure, this may cause damage to the cells at the target site and their neighboring tissues (for example, photoreceptors) and even loss of vision. Thus, the ophthalmic treatment apparatus of FIG. 1 may include a monitoring unit 40 to check in real time how treatment is going by monitoring changes in tissue state during treatment.

The monitoring unit 40 of the present exemplary embodiment may include a plurality of monitoring units 41 and 42 for performing monitoring individually. Specifically, the monitoring unit 40 may include a first monitoring unit 41 and a second monitoring unit 42. The first monitoring unit 41 may measure information on the state of a target site by a first method, and the second monitoring unit 42 may measure information on the state of a target site by a second method. That is, the first monitoring unit 41 and the second monitoring unit 42 are able to make up for the shortcomings of each measurement method.

In an example, the first monitoring unit 41 may be configured using an optoacoustic sensor. The optoacoustic sensor is a apparatus that measures acoustic signals generated by light absorption. As stated above, RPE cells (or trabecular meshwork cells) at a target site undergo state changes as they absorb a treatment beam during treatment, by which acoustic signals are generated. It is understood that these acoustic signals are generated when microbubbles are generated as the temperature of the RPE cells (or trabecular meshwork cells) rise. The first monitoring unit 41 may measure these signals and monitor changes in the state of the target site and how treatment is going.

The first monitoring unit 41 according to the present exemplary embodiment may be placed on the contact lens of the object part 70 and measure acoustic signals transferred from the patient's eye while making contact with the patient's eye. However, this is merely an example, and the first monitoring unit may be configured as a separate apparatus from the contact lens and placed in contact with the patient's eye or a site adjacent to the eye.

Meanwhile, the second monitoring unit 42 may be configured as a reflectometry sensor. The second monitoring unit 42 may receive reflected light from a target site and detect information on the state of the target site included in the reflected light by analyzing the reflected light. Accordingly, it is possible to measure changes in the state of the target site and how treatment is going.

The second monitoring unit 42 of the present exemplary embodiment receives reflected light from a treatment beam directed to a target site. As shown in FIG. 2, some of the treatment beam directed to the target site is absorbed into the target site, and some of it is received by the sensor of the second monitoring unit 42 through the beam combiners 31. The second monitoring unit 42 monitors information on the state of the target site by analyzing the parameters of the received reflected light. For example, as microbubbles are generated in the RPE cells (or trabecular meshwork cells) by a treatment beam, a signal of the reflected light has more frequency components in the range of 5 to 50 MHz. Based on this, the second monitoring unit 42 measures changes in the state of the target site and how treatment is going. It should be noted that other various parameters besides the frequency components contained in the reflected light may be used.

The present exemplary embodiment offers the advantage of monitoring changes made to a target site by a treatment beam in real time since the second monitoring unit 42 performs monitoring using a reflected treatment beam. However, this is merely an example, and monitoring may be performed, not by receiving a treatment beam, but by directing a probe beam for monitoring to a target site and receiving the probe beam reflected from the target site.

As described above, the first monitoring unit according to the present exemplary embodiment is configured as an optoacoustic sensor, and the second monitoring unit is configured as a reflectometry sensor. Besides, the first monitoring unit or the second monitoring unit may be configured using other various sensors. In another example, as shown in FIG. 4, the second monitoring unit may be configured as an interferometry sensor instead of a reflectometry sensor.

Figure 4:
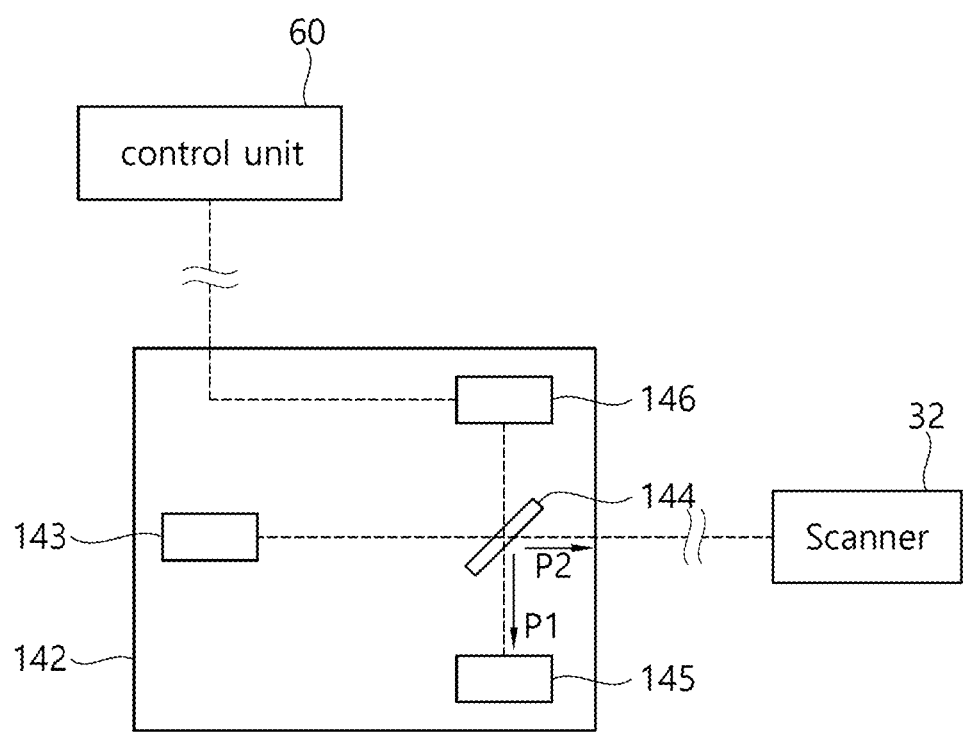
FIG. 4 is a schematic block diagram illustrating a configuration of a second monitoring unit.

FIG. 4 is a schematic block diagram illustrating a configuration of a second monitoring unit according to another example. If the second monitoring unit is configured as an interferometry sensor like an OCT system, the second monitoring unit may use information on interference of light reflected from a target site. Accordingly, it is possible to obtain various tomographic information including the temperature of the target site, changes in the state of the target site, and how treatment is going. While conventional OCT systems acquires a tomographic image of a certain area while scanning from one position to another horizontally (with respect to the surface of the retina at the fundus), the second monitoring unit 142 of FIG. 4 acquires tomographic information of a target site multiple times or continuously during the treatment of that target site. Moreover, since the optical path changes with changes in the tissue state of the target site, interference information sensed by the second monitoring unit 142 may change. Thus, the changes in the state of the target site may be detected based on this change in interference information.

As shown in FIG. 4, the second monitoring unit 142 configured as an interferometry sensor includes a probe light source 143, a beam splitter 144, a reference beam reflector 145, and a detector 146.

The probe light source 143 may be a light source that generates a low coherent beam in the case of SD OCT, and may be a swept source light source capable of changing the wavelength of light in the case of SS OCT.

Light coming from the probe light source 143 is spilt into two beams, i.e., a detection beam and a reference beam as it passes through the beam splitter 144. The reference beam travels along a first path P1, reaches the reference beam reflector 145, and is then reflected from the reference beam reflector 145. The probe beam travels along a second path P2, is directed to a target site through the beam delivery unit 30, and is then reflected from the target site. The reflected probe beam and reference beam are recombined at the beam splitter 144 and directed toward the detector 146.

Here, the probe beam and reference beam recombined by the beam splitter 144 interfere with each other, and the detector 146 detects information on the state of the target site by using information on the interference between the received probe beam and reference beam. The detector 146 may be configured using an array detector in the case of SD OCT, and may be configured using a photo diode in the case of SS OCT.

As such, the second monitoring unit 142 of FIG. 4 is able to detect minute changes in tissue state, including a temperature rise at the target site, change in tissue thickness, change in reflectivity, tissue movement, any unusual occurrence, etc. by using information on interference of the probe beam detected by an interferometer. While FIG. 4 illustrates an example in which an interferometry sensor is used instead of the second monitoring unit, the first monitoring unit may be replaced with an interferometry sensor so that the monitoring unit is configured by using an interferometry sensor and a reflectometry sensor.

As explained above, the first monitoring unit 41 and the second monitoring unit 42 measure changes in the state of a target site in different ways, and deliver this information to the control unit 60. Based on the information measured by the first monitoring unit 41 and second monitoring unit 42, the control unit 60 may control the operation of the treatment apparatus.

The control unit 60 is component that controls the operation of various components, including the treatment beam generation unit 10, aiming beam generation unit 20, and beam delivery unit 30. This way, the treatment site, treatment time, the parameters of treatment beams, etc. may be adjusted variously. To achieve this type of control, the control unit 60 controls various components according to the above information monitored by the monitoring unit 40.

Specifically, the control unit 60 controls a treatment beam such that the treatment beam is directed to the same target site multiple times during the treatment of that target site. If it is detected that the treatment intensity applied during this procedure is not the same as set by the monitoring unit 40, the control unit 60 adjusts the parameters of treatment beams by controlling the treatment beam irradiation unit. In this case, the parameters of treatment beams are adjusted in such a way that the amount of energy delivered per unit area of the target site increases. In an example, the control unit 60 may adjust the parameters of treatment beams in such a way that the output power of treatment beams sequentially increases until the end of the treatment. In contrast, if the monitoring unit detects that the target site is treated with a set treatment intensity, the control unit 60 may finish the treatment of the target site by discontinuing irradiating the target site with a treatment beam. The control by the control unit will be described in more specific details below.

Here, the control unit 60 may make use of the information measured by the first monitoring unit 41 and second monitoring unit 42 in various ways. For example, if the information measured by the first monitoring unit and second monitoring unit both satisfies a first condition, the control unit 60 may determine that the state of the target site reaches the first condition and implement a corresponding control. Alternatively, information on the state of the target site may be detected based on the information measured by either the first monitoring unit or the second monitoring unit. If it is determined that the reliability of reference information is lowered due to an unpredictable event, the state information may be detected by using the information measured by the other monitoring unit.

If any one of the two monitoring units 41 and 42 detects that the treatment of the target site is completed, the control unit 60 of the present exemplary embodiment determines that the treatment of the target site is completed and terminates irradiating that site with a treatment beam. As described previously, it is usual that a change in the state of the RPE cells may lead to the generation of microbubbles or that cell expansion or damage may lead to an optical path change or the generation of scattered light. Exceptionally, even if the state changes, the strength of acoustic wave signal may be weak, or there may be only a slight optical change (for example, there is no substantial change in the optical path, or the amount of reflected scattered light is small). Even in these exceptional cases, the present exemplary embodiment may prevent tissue damage due to an excessive amount of energy delivered to a target site by detecting state changes in different ways and determining the timing of completion of treatment.

Meanwhile, referring to FIGS. 5 and 6, the spot size of a treatment beam directed to a target site, the monitoring method using the monitoring unit, and the control operation based on the spot size and the monitoring method will be described in details below. The description will be given regarding the treatment of the fundus shown in FIG. 2 in order to avoid redundancy; however, the technical characteristics to be described below may also apply to the treatment of the anterior segment of the eye shown in FIG. 3. That is, it should be noted that a target site at the fundus to be explained below may be replaced with TM tissue and a plurality of RPE cells located at the target site may be replaced with a plurality of TM cells.

Figure 5:
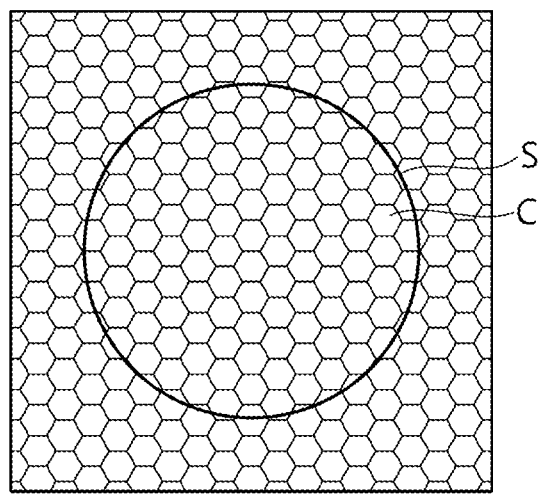
FIG. 5 is a view illustrating the way how a treatment beam is directed to the fundus.

FIG. 5 is a view illustrating the way how a treatment beam is directed to the fundus. As shown in FIG. 5, the spot size of a treatment beam directed to a target site should be enough to ensure that a plurality of RPE cells (C) are located within the boundary (S) of the spot with respect to the RPE cell layer. Accordingly, treatment is performed in such a way that energy is delivered to the plurality of RPE cells located at a target site during the treatment of that target site, and the monitoring unit 40 may monitor how the treatment is going by detecting changes in the state of the plurality of RPE cells.

The RPE cells exposed to the treatment beam remain as they are unless an enough amount of energy is delivered to them, or are replaced with new RPE cells due to state changes if an enough amount of energy is delivered to them. Since one RPE cell follows one of these two processes when irradiated with the treatment beam, it is difficult to adjust treatment intensity if the treatment beam is focused to a spot size that covers only one RPE cell. In contrast, if the treatment beam is configured to deliver energy to a plurality of RPE cells, as in the present exemplary embodiment, the treatment intensity may be adjusted by adjusting the amount of RPE cells whose state is changed by treatment, out of the plurality of RPE cells. Therefore, according to the present exemplary embodiment, it is possible to perform treatment with an optimum treatment intensity depending on the type of disease, the treatment site, and the patient's condition. Needless to say, it is possible to adjust the treatment intensity by adjusting the intervals of target sites where the treatment beam is directed, even when delivering energy to only one RPE cells corresponding to the spot size of the treatment beam. However, this increases the treatment time. Moreover, because the size of RPE cells varies with their position on the retina (e.g., the RPE cells at the central part of the fundus have a diameter of 10 to 15 μm, and the RPE cells at the periphery of the fundus have a diameter of 50 μm or greater), many factors should be taken into consideration for control, including adjusting the intervals between target sites depending on the treatment area, in order to maintain uniform treatment intensity.

As such, if the treatment beam has a small spot size, treatment time increases and treatment intensity cannot be varied. On the contrary, if the treatment beam has a too large spot size, it is difficult to treat local lesions and target sites close to blood vessels or the macula. Thus, the spot size (S) of the treatment beam may be configured to cover 10 to 1,000 RPE cells (C), preferably 50 to 500 RPE cells, within the boundary of a spot with respect to an area in which RPE cells are irradiated. Alternatively, the spot size (S) of the treatment beam may have a diameter of 50 μm to 1,000 μm.

In the present exemplary embodiment, the spot size of the treatment beam may have a diameter of 100 μm to 400 μm.

Further, the spot size may be adjusted depending on the treatment area. For example, if the treatment area is located inside the fundus, the spot diameter may be controlled to range from 150 to 200 µm, and if the treatment area is located at the periphery of the fundus, the spot diameter may be controlled to range from 250 to 350 µm.

This way, the monitoring unit 40 monitors in real time how the treatment of a target site is working, while a plurality of RPE cells located at the target site are being irradiated with a treatment beam. Here, the monitoring unit 40 may monitor how the treatment is going by detecting the amount or proportion of RPE cells whose state has changed, out of the plurality of RPE cells, and the control unit 60 may determine the treatment intensity applied to the target site based on the monitoring result.

Figure 6:
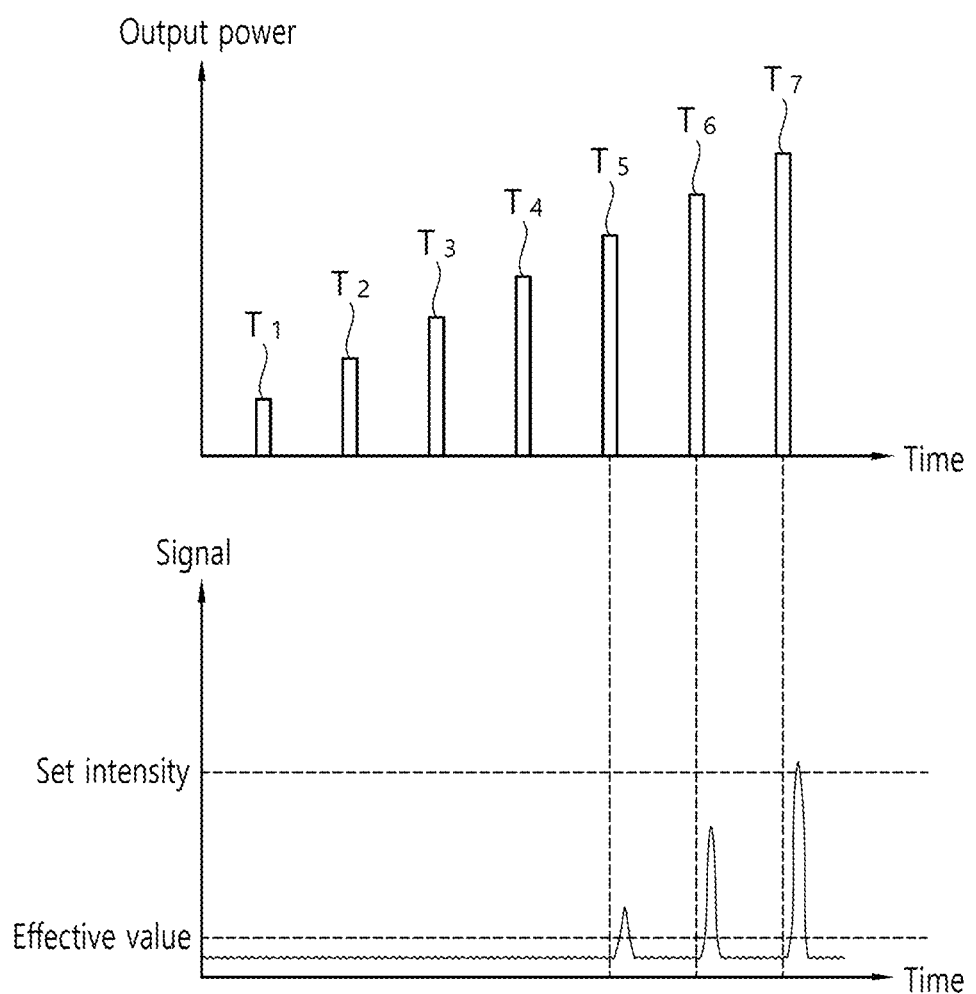
FIG. 6 is a graph illustrating a treatment beam irradiation pattern and a corresponding signal measured by a monitoring unit.

FIG. 6 is a graph illustrating a treatment beam irradiation pattern and a corresponding signal measured by a monitoring unit. As shown in the graph in the upper part of FIG. 6, the treatment beam irradiation unit irradiates a target site with a treatment beam multiple times, and each treatment beam is emitted in such a way that the output power sequentially increases. In the meantime, the signal measured by the monitoring unit is shown in the graph in the lower part of FIG. 6 (the signal measured by the first monitoring unit is illustrated for convenience of description).

As shown in FIG. 6, a measured value lower than an effective value is detected by the monitoring unit 40 while a treatment beam is emitted four times (T1 to T4). The measured value detected during this period is a noise that is detected under a normal condition. Accordingly, the control unit 60 determines that there is no change in the state of RPE cells while a measured value lower than the effective value is detected.

At the time when a fifth treatment beam T5 is emitted, the monitoring unit 40 detects a measured value equal to or higher than the effective value, and the control unit 60 therefore determines that some RPE cells at the target site begin to change in state. When a sixth treatment beam T6 and a seventh treatment beam T7 are emitted, the value measured by the monitoring unit 40 gradually increases, and the control unit 60 therefore determines that the amount of RPE cells whose state has changed gradually increases.

As such, as the output power of treatment beams becomes higher, the amount or proportion of RPE cells whose state has changed increases and therefore the values measured by the monitoring unit 40 increases too. Here, the treatment intensity may be set by the amount or proportion of RPE cells whose state has changed, out of the plurality of RPE cells located at the target site. The control unit 60 may set the treatment intensity by matching the value measured by the monitoring unit 40 to data stored in memory. This way, the control unit 60 may determine, in real time, how the treatment of the target site is working during treatment beam irradiation. Also, if the value measured by the monitoring unit 40 exceeds a value corresponding to the set treatment intensity (the measured value for T7 of FIG. 6), the control unit 60 determines that the treatment has been performed with the set intensity for the corresponding site, and finishes the treatment of that site.

Meanwhile, as shown in FIG. 1, the ophthalmic treatment apparatus 1 may further include a setting unit 80 for allowing the user to select a treatment mode. The setting unit 80 includes a display and manual operation buttons the user can manipulate. The selected treatment mode includes information on treatment intensity, and also may include information on various parameters such as a treatment beam irradiation pattern. Accordingly, when the user selects a treatment mode through the setting unit 80, the control unit 60 controls the components to perform the corresponding treatment based on the selected treatment mode.

Figure 7:
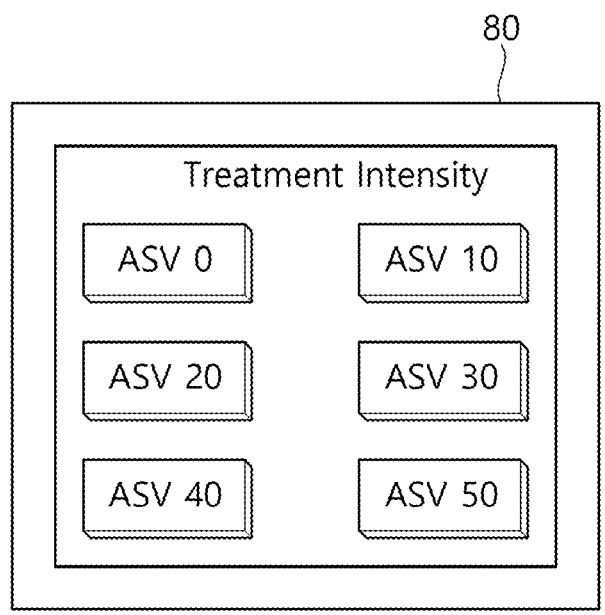
FIG. 7 illustrates an example of what is shown through a display of a setting unit.

FIG. 7 illustrates an example of what is shown through a display of a setting unit. The setting unit 80 of FIG. 7 is configured to select a treatment intensity for each target site which works as a sort of treatment mode. In an example, the treatment intensity may be represented by the proportion of RPE cells (or TM cells) whose state is changed by treatment, out of the plurality of RPE cells (or TM cells) located at the target site.

In FIG. 7, ASV 20 (auto-set value 20) represents the treatment intensity with which about 20% of the plurality of cells (RPE cells or TM cells) located at the target site can change in state, and ASV 50 represents the treatment intensity with which about 50% of them can change in state. Once the treatment intensity is set, the control unit 60 emits a treatment beam for each target site using the monitoring unit 40 until the treatment is performed as the set treatment intensity.

Figure 8:
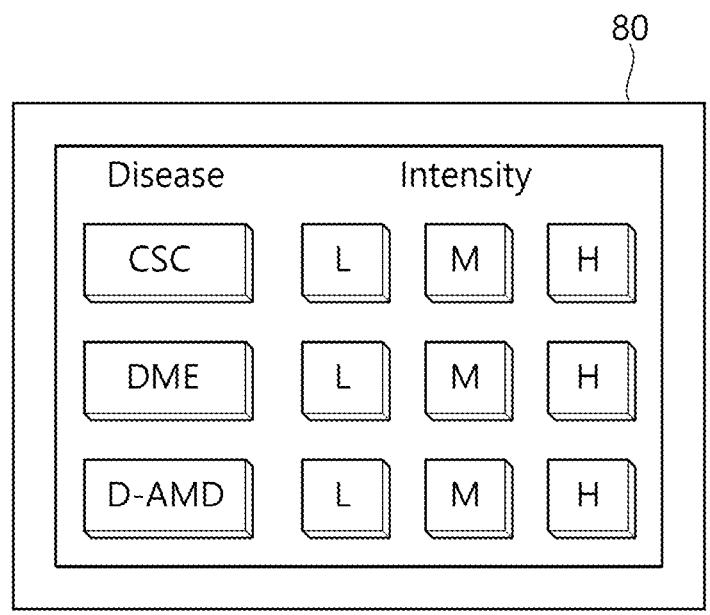
FIG. 8 illustrates another example of what is shown through the display of the setting unit.

FIG. 8 illustrates another example of what is shown through the display of the setting unit. The setting unit 80 of FIG. 8 shows the names of diseases to be treated as treatment modes. For example, if the ophthalmic treatment apparatus is configured for use in treating diseases of the fundus, the setting unit may display typical diseases of the fundus, such as central serous chorioretinopathy (CSC), diabetic macular edema (DME), and dry age-related macular degeneration (Dry AMD). Thus, the user can select a treatment mode for a patient's disease they want to treat.

The treatment modes in FIG. 8 each may include information on different treatment intensities. For example, the results of a clinical trial showed that CSC can be treated with a low treatment intensity because the RPE cells are relatively healthy, and that DME should be treated with a high treatment intensity because the RPE cells are in bad state. Also, the results showed that Dry AMD can be treated with a treatment intensity higher than that of SCS and lower than that of DME. Thus, once the user selects a treatment mode based on the disease to be treated, treatment is performed with a treatment intensity suitable for that disease.

For example, if the CSC mode is selected, the treatment intensity may be set to range from ASV 20 to ASV 40, if the Dry AMD mode is selected, the treatment intensity may be set to range from ASV 40 to ASV 60, and if the DME mode is selected, the treatment intensity may be set to range from ASV 60 to ASV 80. Further, as shown in FIG. 8, the treatment intensity for each disease may be split into three levels: high, medium, and low, so as to subdivide the treatment intensity within the range of treatment intensity for each disease.

Although FIG. 8 illustrates treatment modes for diseases of the fundus, treatment modes for various diseases of the anterior segment of the eye, including glaucoma, may be displayed if the ophthalmic treatment apparatus is configured as a apparatus for treating diseases of the anterior segment of the eye.

This way, the ophthalmic treatment apparatus 1 of the present exemplary embodiment may be configured to focus a treatment beam to a spot size that covers a plurality of RPE cells, so that treatment is performed at different treatment intensities depending on which treatment mode the user selects. Moreover, the monitoring unit 40 is able to perform a safe and optimum treatment by monitoring information on the state of a target site in different ways by using a plurality of monitoring units 41 and 42.

Figure 9:
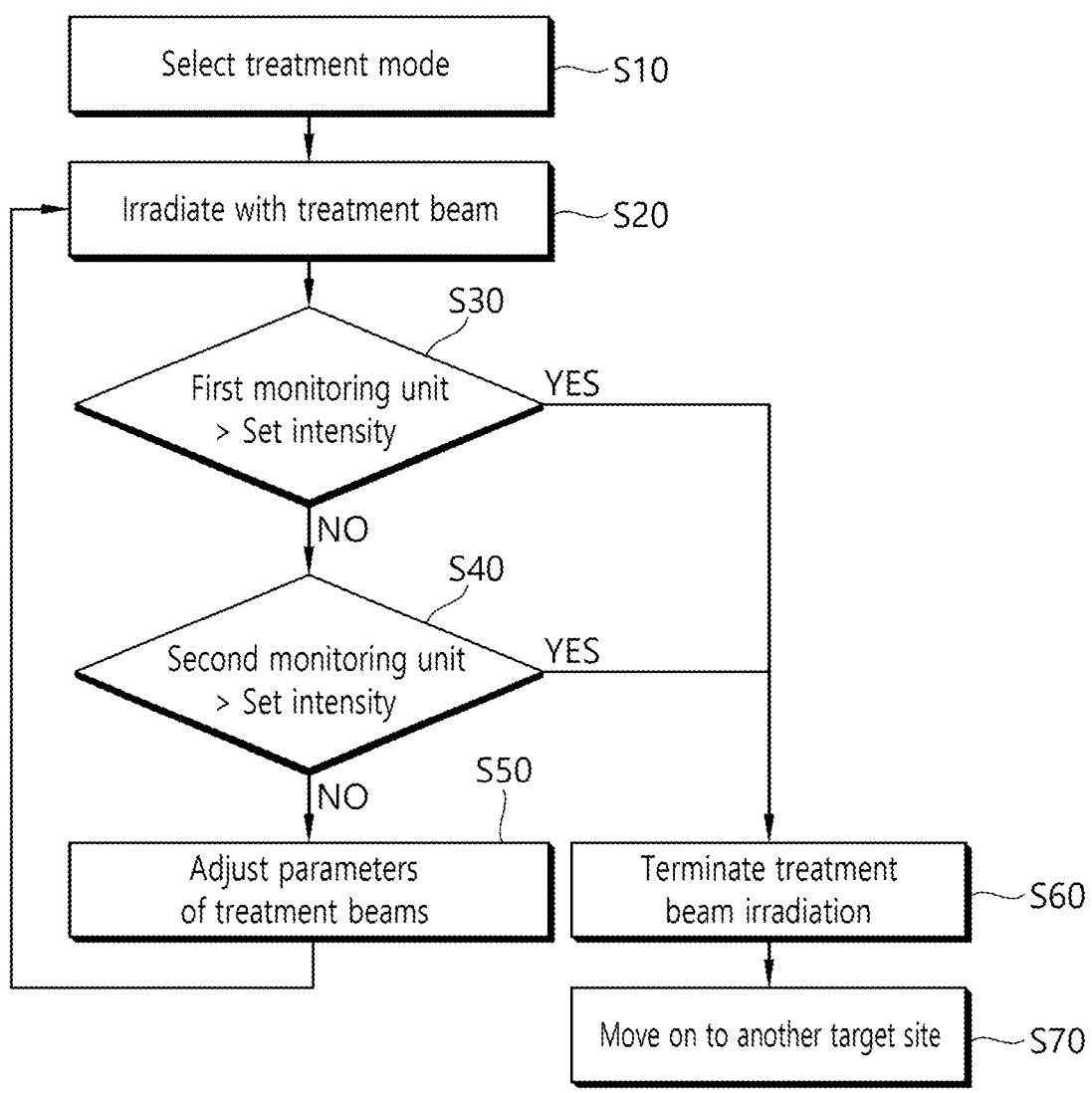
FIG. 9 is a sequential diagram illustrating a control method for the ophthalmic treatment apparatus of FIG. 1.

FIG. 9 is a sequential diagram illustrating a control method for the ophthalmic treatment apparatus of FIG. 1. Hereinafter, the control method for the above-described ophthalmic treatment apparatus 1 will be described in detail with reference to FIG. 9.

When a treatment area is selected depending on a patient's disease, treatment is performed after fixing the anterior segment of the patient's eye to the object part 70. The treatment is performed by irradiating a plurality of target sites distributed within the treatment area with treatment beams. Here, the treatment is performed in such a way that a plurality of treatment beams are directed to one target site and then move on to another target site after the treatment of the previous target site is completed. In FIG. 9, the description will be given regarding a treatment procedure for the first target site for ease of comprehension.

To perform a treatment, the user selects a treatment mode through the setting unit 80 (S10), and information on the selected treatment mode is delivered to the control unit 60. Based on the selected treatment mode, the control unit 60 runs the treatment beam irradiation unit to irradiate with a treatment beam (S20).

When a treatment beam is emitted, the monitoring unit 40 performs the step of monitoring information on the state of a target site. At this time, the first monitoring unit 41 and the second monitoring unit 42 individually monitor information on the state of the target site.

During the monitoring step, the control unit 60 determines whether the treatment is performed with a set treatment intensity, based on the information monitored by the first monitoring unit 41 (S30). Also, the control unit 60 determines whether the treatment is performed with a set treatment intensity, based on the information monitored by the second monitoring unit 42 (S40). Although FIG. 9 illustrates that the determination step S30 using the first monitoring unit and the determination step S40 using the second monitoring unit are sequentially carried out, they are not always carried out in this order. The two steps S30 and S40 may be carried out simultaneously at an interval corresponding to a treatment beam irradiation period, or may be carried out consecutively during the treatment.

If it is determined that the set treatment intensity is not reached in both the determination step S30 using the first monitoring unit and the determination step S40 using the second monitoring unit, the control unit 60 determines that the treatment of the target site is not completed, and adjusts the parameters of treatment beams (S50). Here, the parameters of treatment beams are adjusted in such a way that the amount of energy delivered per unit area of the target site by treatment beams sequentially increases; for example, the output power of treatment beams, which is one of the parameters, may be increased. Afterwards, the control unit 60 irradiates the target site with a treatment beam whose parameters are adjusted, and repeats the above steps.

If it is determined that the set treatment intensity is reached in any one of the determination step S30 using the first monitoring unit and the determination step S40 using the second monitoring unit, the control unit 60 determines that the treatment of the target site is completed. Thus, the control unit 60 terminates irradiating the target site with a treatment beam (S60), moves on to another target site, and repeats the above steps S20 through S70.

Hereinafter, an ophthalmic treatment apparatus and a control method therefor according to a second exemplary embodiment of the present invention will be described with reference to FIG. 10 and FIGS. 11 to 13. In describing the present exemplary embodiment, the same or similar components or steps as the foregoing first exemplary embodiment will be replaced with those in the drawings and description of the first exemplary embodiment in order to avoid redundancy.

The first monitoring unit and second monitoring unit of the monitoring unit of the foregoing first exemplary embodiment are used for the purpose of monitoring how treatment is going. On the other hand, in the present exemplary embodiment, information measured by each monitoring unit may be used for different control purposes by taking into consideration the characteristics of different measurement methods of the first monitoring unit 41 and second monitoring unit 42.

As described above, the first monitoring unit 41 is a component that receives acoustic wave signals generated from a target site, converts them into electrical signals, and delivers them to the control unit 60, which does not require complicated operations and therefore has a relatively fast processing speed. However, the first monitoring unit 41 has a relatively low accuracy because information detected by the first monitoring unit 41 may contain a signal of an event that has occurred at sites other than the target site.

On the contrary, the second monitoring unit 42 is able to accurately detect information on the state of a target site, as compared to the first monitoring unit, since it uses light reflected from the target site. However, the second monitoring unit 42 has a slow operation speed than the first monitoring unit because it undergoes a variety of operational processes in order to detect changes in the parameters of reflected light (the processing speed is relatively slow, especially when the second monitoring unit is configured as an interferometry sensor as shown in FIG. 4, because an interference signal needs to be analyzed through a complicated operational process such as Fourier Transform).

Accordingly, the ophthalmic treatment apparatus of the present exemplary embodiment may use information detected by the first monitoring unit 41 to determine how the treatment is going or the timing of completion of the treatment of the target site, by taking into consideration the fast operation speed of the first monitoring unit 41. Also, information detected by the second monitoring unit 42 may be used to determine if something unusual (an odd event) occurs during the treatment, by taking the accuracy of the second monitoring unit 42 into consideration.

The control unit 60 determines how the treatment is going (for example, which one of the cells at the target site begins to produce microbubbles, the proportion of cells with microbubbles out of the cells at the target site, etc.; here, the cells refer to RPE cells or TM cells) and the timing of completion of treatment, based on information measured by the first monitoring unit 41. The timing of completion of treatment may be determined based on whether a value measured by the first monitoring unit (hereinafter, a first measured value) reaches a first reference value (corresponding to the set treatment intensity) or not. If it is determined that the treatment is completed, the control unit may terminate irradiating the target site with a treatment beam, move on to another target site, and perform treatment. As such, the first monitoring unit may detect, in real time, changes in the state of a target site caused by each treatment beam through fast operations and make use of this information for control purposes.

Meanwhile, as described previously, the second monitoring unit 42 may continuously monitor if there is any unusual occurrence at the target site during the treatment. Here, the unusual occurrence may include various events. For example, it may include when the RPE cells or TM cells are altered by a treatment beam by an abnormal mechanism, when something unusual occurs to the surface tissue of the retina, when something unusual occurs to other tissues of the anterior segment of the eye, and so on.

The second monitoring unit 42 is able to acquire high-accuracy information on the target site (it can even detect individual events occurring in tissue at different depths as well as in the RPE cells (or TM cells) at the target site, especially if the second monitoring unit is configured as an interferometry sensor as shown in FIG. 4). Thus, if a measured value (hereinafter, a second measured value) is higher than a second reference value (a value corresponding to an unusual occurrence) based on information measured by the second monitoring unit 42, the control unit 60 may determine that something unusual has occurred.

Here, the second measured value may be a value that is obtained by processing information acquired by the second monitoring unit in various ways. For example, the second reference value may be a value obtained by the second monitoring unit. Alternatively, the second reference value may be the difference between the second measured value and previously measured values obtained during multiple measurements made by the second monitoring unit.

If it is determined that something unusual has occurred, based on information measured by the second monitoring unit 42, the control unit 60 may immediately stop the treatment beam irradiation, regardless of information measured by the first second monitoring unit 41. Also, the control unit 60 may indicate this externally through an indicating unit 90 (see FIG. 1) to inform the user of an unusual occurrence.

Figure 10:
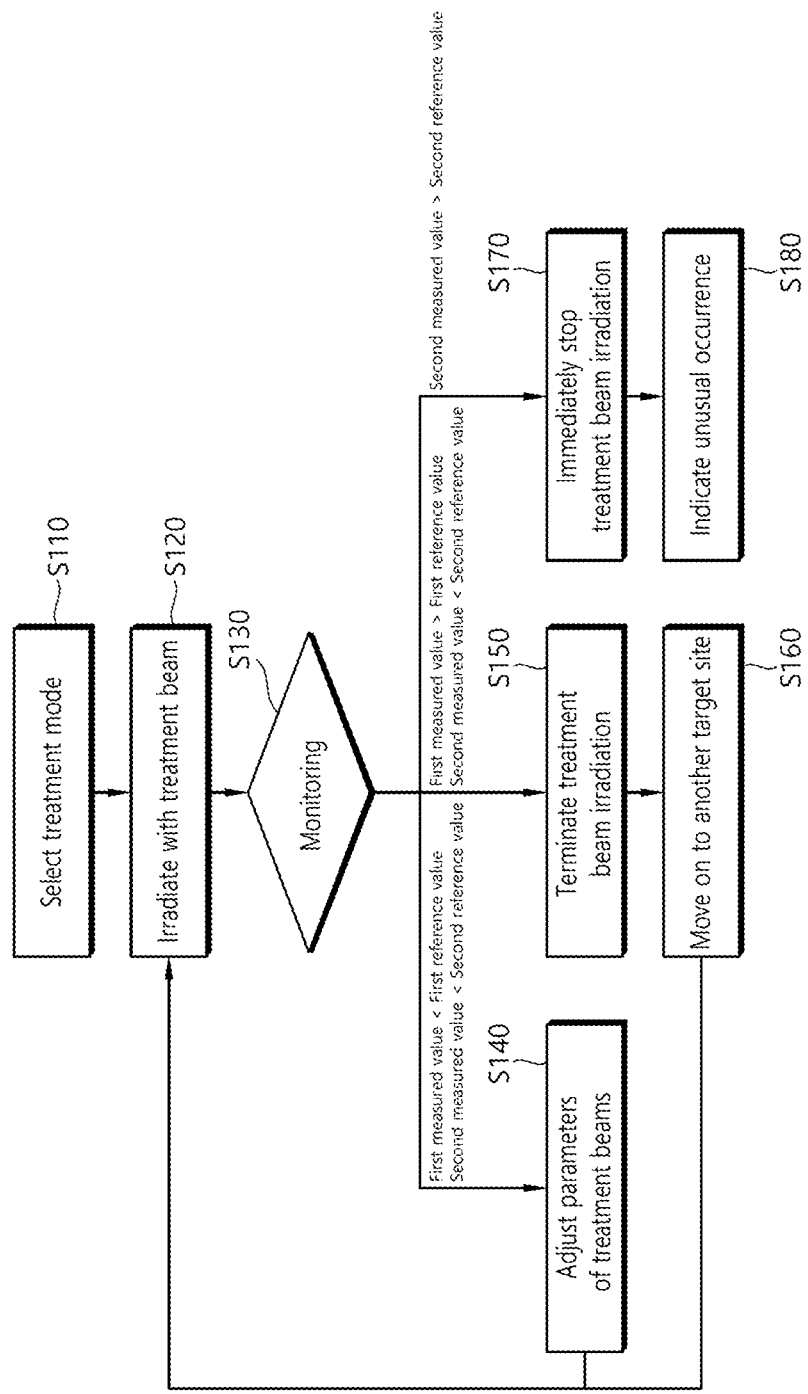
FIG. 10 is a sequential diagram illustrating a control method for an ophthalmic treatment apparatus according to a second exemplary embodiment of the present invention.

FIG. 10 is a sequential diagram illustrating a control method for an ophthalmic treatment apparatus according to a second exemplary embodiment of the present invention. Hereinafter, a control method for the above-described ophthalmic treatment apparatus 1 will be described in detail with reference to FIG. 10.

In a control method for an ophthalmic treatment apparatus according to the present exemplary embodiment, a treatment mode is selected (S110), and a target site is irradiated with a treatment beam (S120), like in the first exemplary embodiment.

When a treatment beam is emitted, the first monitoring unit 41 and the second monitoring unit 42 monitor information on the state of a target site. While FIG. 10 illustrates that the monitoring step S130 precedes the treatment beam irradiation step 120, these steps are not always carried out in this order but may be carried out consecutively during treatment.

If this step shows that a first measured value obtained by the first monitoring unit 41 is lower than a first reference value, the control unit 60 determines that the treatment of the target site is not complete, and adjusts the parameters of treatment beams (S140). For example, the output power of treatment beams, which is one of the parameters, may be increased. Afterwards, the control unit 60 controls the treatment beam irradiation unit to irradiate the target site with a treatment beam whose parameters are adjusted (S120). As long as the first measured value is lower than the first reference value, the steps S120 through S140 are repeated, whereby the target site is irradiated with a treatment beam multiple times.

If the first measured value obtained by the first monitoring unit 41 is higher than the first reference value, the control unit 60 determines that the treatment of the target site is completed. Thus, the control unit 60 terminates irradiating the target site with a treatment beam (S150), moves on to another target site, and repeats the above steps.

In the above-described process, the second monitoring unit 42 may continuously monitor if there is any unusual occurrence, and perform the above steps S120 through S160 if a second measured value obtained by the second monitoring unit 42 is lower than a second reference value.

On the other hand, if a value measured by the second monitoring unit 42 is higher than the second reference value, the control unit 60 determines that something unusual has occurred, and immediately stop the treatment of the target site by discontinuing the treatment beam irradiation (S170). This step is performed immediately after detecting any unusual occurrence, regardless of whether the first measured value is higher or lower than the first reference value. Also, the control unit 60 informs the user of an unusual occurrence through the indicating unit 90 (S180).

Figure 11:
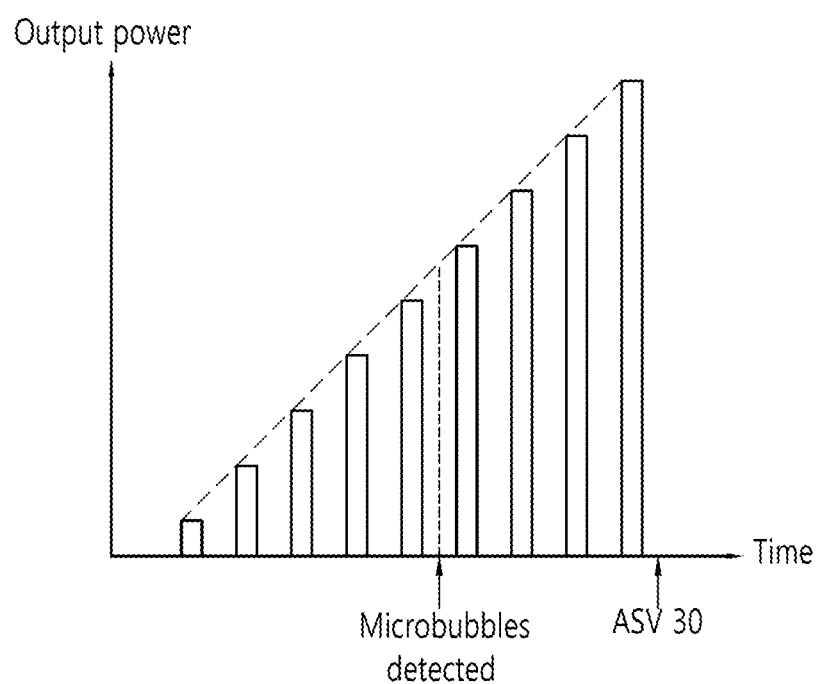
FIGS. 11 through 13 are graphs illustrating a treatment beam irradiation pattern according to the control method of FIG. 10.
Figure 12:
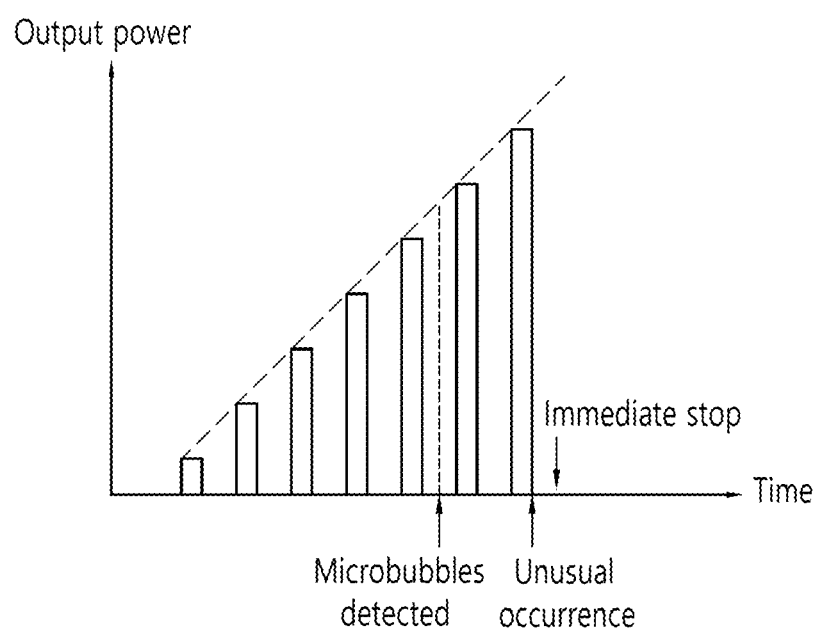
Figure 13:
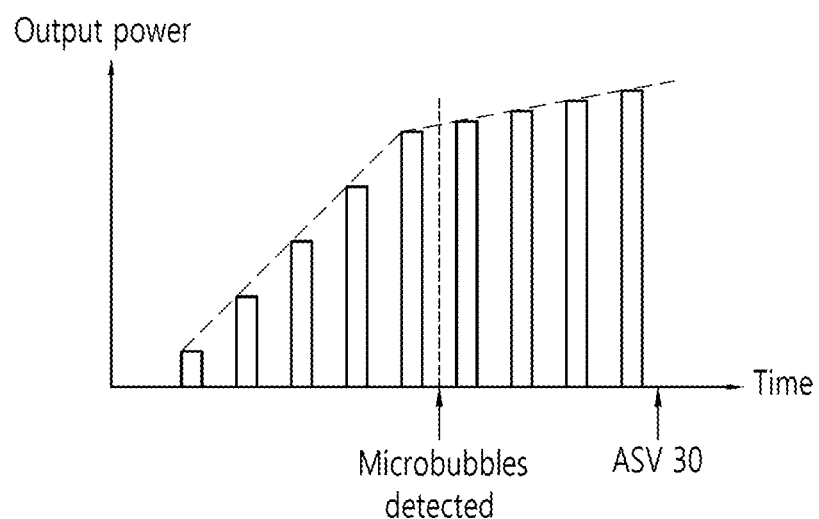

FIGS. 11 through 13 are graphs illustrating a treatment beam irradiation pattern according to the control method of FIG. 10. In FIG. 11, at the time when a fifth treatment beam T5 is emitted, it is detected that microbubbles are generated in RPE cells (or TM cells) at a target site (ASV 0). Whether microbubbles are generated or not is determined based on the first measured value obtained by the first monitoring unit. As described above, if the first measured value is lower than an effective value, it is determined that there is no change in the state of the RPE cells (or TM cells)—that is, microbubbles are not generated, and if the first measured value is equal to or higher than the effective value, it is determined that at least one RPE cell (or TM cell) begins to change in state.

Meanwhile, if the user selects a treatment mode with a treatment intensity of ASV 30, steps S120 to S140 is repeatedly performed S140 until the first measured value exceeds a reference value for ASV 30. In this process, the control unit 60 may determine, in real time, the proportion of RPE cells (or TM cells) whose state is changed by treatment, out of the RPE cells (or TM cells) at the target site, based on the first measured value obtained in real time.

FIG. 11 shows that the first measured value exceeds the reference value for ASV 30 after a ninth treatment beam is emitted, and therefore the control unit 60 may determine that the treatment of the target site is completed and terminate the treatment beam irradiation.

It should be noted that FIG. 11 illustrates that no unusual occurrence is detected during treatment, whereas FIG. 12 illustrates that an unusual occurrence is detected during treatment. Specifically, FIG. 12 illustrates that an unusual occurrence is detected by the second monitoring unit 42 at the time when a seventh treatment beam is emitted. In this case, the control unit terminates the treatment beam irradiation immediately after detecting any unusual occurrence, and finishes the treatment.

Meanwhile, FIGS. 11 and 12 show that the parameters of treatment beams are adjusted in such a way that the output power of treatment beams ramps at the same rate. However, this is merely an example, and the ramp rate of the output power of treatment beams is adjusted to be lower than before detection of microbubbles.

Meanwhile, FIG. 6 and FIGS. 11 through 13 illustrate how to increase the output power of treatment beams when adjusting the parameters of treatment beams. However, this is merely an example, and parameters other than output power may be adjusted to increase the amount of energy delivered per unit area by treatment beams.

Figure 14:
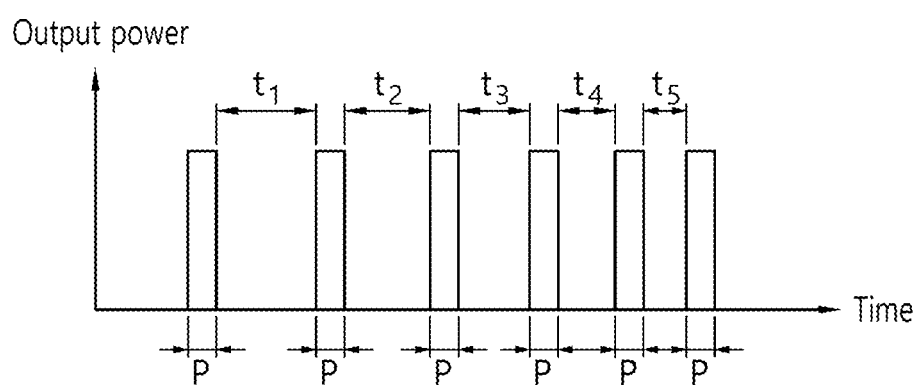
FIGS. 14 through 16 are graphs illustrating another example of adjusting the parameters of treatment beams.
Figure 15:
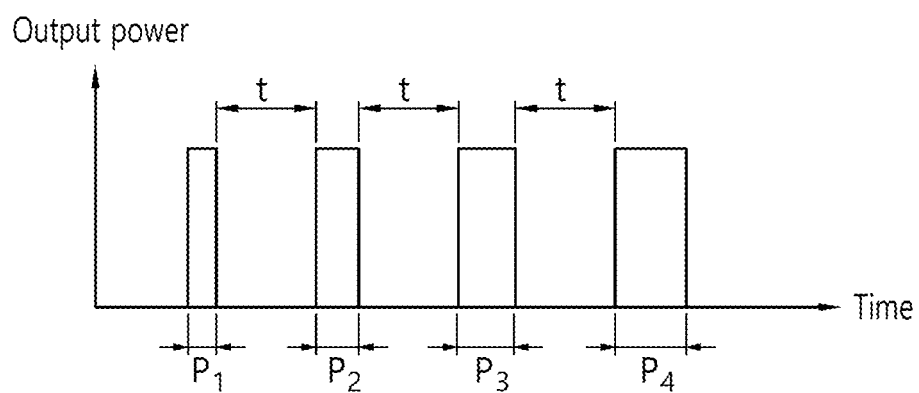
Figure 16:
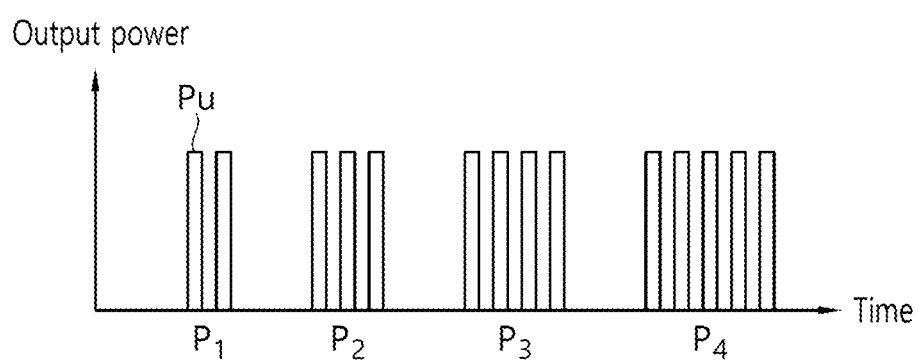

FIGS. 14 through 16 are graphs illustrating another example of adjusting the parameters of treatment beams. As shown in FIG. 14, the treatment beam generation unit generates treatment beams with the same pulse duration time, and the parameters may be adjusted in such a way as to gradually decrease the off time between each treatment beam. Alternatively, as shown in FIG. 15, treatment beam pulses with the same output power are generated, and the parameters may be adjusted in such a way as to gradually increase the pulse duration time of each treatment beam. Besides, as shown in FIG. 16, treatment beams each consisting of a plurality of unit pulses (Pu) may be emitted, and the parameters may be adjusted in such a way as to sequentially increase the number of unit pulses of each treatment beam.

In the above, an ophthalmic treatment apparatus including two monitoring units and a control method therefor have been described in details. It is apparent that the foregoing exemplary embodiments are a simplified description of the present invention, and that these exemplary embodiments may be modified and embodied in various other ways. Although the foregoing description has been made with respect to an ophthalmic treatment apparatus for treating diseases of the fundus and a control method therefor, this is merely an example, and the present invention may be applied to an ophthalmic treatment apparatus for treating glaucoma and a control method therefor. Besides, the present invention may be applied to the treatment of various eye diseases by targeting various tissues in the eyeball.

The invention claimed is:

1. An ophthalmic treatment apparatus comprising:
   a setting unit configured to set a treatment mode;
   a treatment beam irradiation unit for irradiating a target site of the eye with a treatment beam multiple times so as to perform treatment;
   a monitoring unit for monitoring information on a tissue state of the target site caused by the treatment beam during the treatment beam irradiation; and
   a control unit for determining whether a set treatment intensity according to the treatment mode is reached, by using the information monitored by the monitoring unit, and for controlling an operation of the treatment beam irradiation unit on the basis of the determination,
   wherein the monitoring unit comprises a first monitoring unit for detecting change in the tissue state of the target site in real time during the treatment and a second monitoring unit for detecting an abnormal occurrence during the treatment, the first monitoring unit has a processing speed higher than that of the second monitoring unit, the second monitoring unit has an accuracy higher than that of the first monitoring unit, and the information comprises a first measured value obtained by the first monitoring unit and a second measured value obtained by the second monitoring unit, and
   wherein the control unit is configured to determine whether the treatment on the target site is completed based on comparison of the first measured value to a first reference value, and configured to discontinue the operation of the treatment beam irradiation unit based on comparison of the second measured value to a second reference value, regardless of whether the treatment on the target site is completed or not.

2. The ophthalmic treatment apparatus of claim 1, wherein the first monitoring unit and the second monitoring unit monitor the information on the tissue state of the target site in different ways.

3. The ophthalmic treatment apparatus of claim 1, wherein the first monitoring unit and the second monitoring unit respectively monitor the information on the tissue state corresponding to each treatment beam.

4. The ophthalmic treatment apparatus of claim 1, wherein the first monitoring unit is one of a group comprising an optoacoustic sensor, a reflectometry sensor and an interferometry sensor, and the second monitoring unit is other one of the group, which is different from the first monitoring unit.

5. The ophthalmic treatment apparatus of claim 1, wherein the control unit is configured to adjust parameter of the treatment beam in such a way that an amount of energy delivered per unit area of the target site increases, when it is determined that the first measured value and the second measured value are lower than the first reference value and the second reference value, respectively.

6. The ophthalmic treatment apparatus of claim 1, wherein the control unit is configured to terminate the irradiating of the target site, when it is determined that the first measured value is higher than the first reference value and the second measured value is lower than the second reference value.

7. The ophthalmic treatment apparatus of claim 1, wherein the control unit is configured to determine that something unusual has occurred and immediately stop the treatment of the target site, when it is determined that the second measured value is higher than the second reference value.

8. The ophthalmic treatment apparatus of claim 1, wherein the setting unit is configured to indicate a plurality of treatment intensity of different values and allow a user to select a treatment intensity to set the treatment mode.

9. The ophthalmic treatment apparatus of claim 8, wherein the treatment intensity indicated on the setting unit represents the proportion of cell whose state is to be changed, out of a plurality of cells located at the target site.

10. The ophthalmic treatment apparatus of claim 1, wherein the setting unit is configured to indicate a plurality of disease to be treated and allow a user to select a disease to set the treatment mode, and the treatment intensity or an adjustable range of the treatment intensity is determined based on the diseases selected via the setting unit.

11. The ophthalmic treatment apparatus of claim 1, further comprising an object part provided at an end of the treatment beam irradiation unit and including a contact lens,
    wherein the first monitoring unit is placed on the contact lens to measure signals transferred from a patient's eye while contacting the patient's eye.

12. A control method for an ophthalmic treatment apparatus, the control method comprising:
    selecting a treatment intensity through a setting unit;
    irradiating a target site of an eye with a treatment beam, using a treatment beam irradiation unit to perform treatment on the target site, the target site being a tissue with a plurality of cell located at the target site;
    monitoring information on changes in a state of the plurality of cells located at the target site through a monitoring unit, the information including a first measured value and a second measured value, the first measured value obtained by a first monitoring unit for detecting change in the tissue state of the target site in real time during treatment and the second measured value obtained by a second monitoring unit for detecting an abnormal occurrence during the treatment, the first monitoring unit having a processing speed higher than that of the second monitoring unit, the second monitoring unit having an accuracy higher than that of the first monitoring unit;

determining whether a set treatment intensity is reached or whether an abnormal situation occurs, based on the first measured value and the second measured value;

determining whether the treatment on the target site is completed based on comparison of the first measured value to a first reference value; and discontinuing an operation of the treatment beam irradiation unit based on comparison of the second measured value to a second reference value, regardless of whether the treatment on the target site is completed or not.

13. The control method of claim 12, wherein the first monitoring unit and the second monitoring unit monitor the information on the tissue state of the target site in different ways.

14. The control method of claim 12, wherein the treatment beam is irradiated multiple times on a same target site, and the first measured value and the second measured value corresponding to each treatment beam are respectively obtained multiple times.

15. The control method of claim 12, wherein controlling the operation of the treatment beam irradiation unit includes adjusting parameters of the treatment beam in such a way that an amount of energy delivered per unit area of the target site increases, when it is determined that the first measured value and the second measured value are lower than the first reference value and the second reference value, respectively.

16. The control method of claim 12, wherein controlling the operation of the treatment beam irradiation unit includes terminating the irradiating of the target site, when it is determined that the first measured value is higher than the first reference value and the second measured value is lower than the second reference value.

17. The control method of claim 12, wherein controlling the operation of the treatment beam irradiation unit includes determining that something unusual has occurred and immediately stopping the treatment of the target site, when it is determined that the second measured value is higher than the second reference value.

18. The ophthalmic treatment apparatus of claim 1, wherein the first monitoring unit is an optoacoustic sensor, and the second monitoring unit is either a reflectometry sensor or an interferometry sensor.

19. The ophthalmic treatment apparatus of claim 1, wherein the control unit is configured to immediately discontinue the operation of the treatment beam irradiation unit when the second measured value is higher than the second reference value, even if the treatment on the target site is not completed.

20. The ophthalmic treatment apparatus of claim 19, wherein the control unit is configured to determine that the treatment is not completed and adjust parameter of the treatment beam in such a way that an amount of energy delivered per unit area of the target site increases, when the first measured value and the second measured value are lower than the first reference value and the second reference value, respectively, and wherein the control unit is configured to determine that the treatment is completed and terminate the irradiating of the target site, when the first measured value is higher than the first reference value and the second measured value is lower than the second reference value.

* * * * *